United States Patent
Ng et al.

(10) Patent No.: US 10,677,790 B2
(45) Date of Patent: Jun. 9, 2020

(54) OPTOCHEMICAL DETECTOR AND A METHOD FOR FABRICATING AN OPTOCHEMICAL DETECTOR

(71) Applicant: City University of Hong Kong, Kowloon (HK)

(72) Inventors: Siu Pang Ng, Kowloon (HK); Chi-man Lawrence Wu, Kowloon (HK); Guang-yu Qiu, Kowloon (HK); Hui Lun Anton Law, New Territories (HK)

(73) Assignee: City University of Hong Kong, Kowloon (HK)

( * ) Notice: Subject to any disclaimer, the term of this patent is extended or adjusted under 35 U.S.C. 154(b) by 517 days.

(21) Appl. No.: 15/214,828

(22) Filed: Jul. 20, 2016

(65) Prior Publication Data

US 2018/0024127 A1 Jan. 25, 2018

(51) Int. Cl.
| | |
|---|---|
| *G01N 21/552* | (2014.01) |
| *B01L 3/00* | (2006.01) |
| *G01N 33/543* | (2006.01) |
| *G01J 3/45* | (2006.01) |
| *G01N 33/84* | (2006.01) |

(52) U.S. Cl.
CPC .. *G01N 33/54373* (2013.01); *B01L 3/502715* (2013.01); *G01J 3/45* (2013.01); *G01N 21/553* (2013.01); *G01N 21/554* (2013.01); *G01N 33/84* (2013.01)

(58) Field of Classification Search
None
See application file for complete search history.

(56) References Cited

U.S. PATENT DOCUMENTS 4,377,343 A * 3/1983 Monson ............... G01B 9/02
244/130
6,485,703 B1 * 11/2002 Cote ............... A61K 49/0041
424/9.1

(Continued)

FOREIGN PATENT DOCUMENTS

| CN | 1536355 A | 10/2004 |
| CN | 102135518 A | 7/2011 |

(Continued)

OTHER PUBLICATIONS

World Health Organization. (2003): Lead in Drinking Water. Background Document for Development of WHO Guidelines for Drinking Water Quality. WHO/SDE/WSH/03.04/09/Rev/1.

(Continued)

*Primary Examiner* — Jill A Warden
*Assistant Examiner* — Neil Turk
(74) *Attorney, Agent, or Firm* — Renner Kenner Greive Bobak Taylor & Weber

(57) ABSTRACT

An optochemical detector and a method for fabricating an optochemical detector includes a light generation unit arranged to emit a light signal; a probe cell unit arranged to alter at least one physical characteristic of the light signal in response to an interaction with a target substance; and a light detection unit arranged to receive the light signal altered by the probe cell unit; wherein a detection of the target substance is characterized by a change in the at least one physical characteristic altered by the probe cell unit.

30 Claims, 6 Drawing Sheets

(56) References Cited

U.S. PATENT DOCUMENTS

| | | | |
|---|---|---|---|
| 6,570,657 B1* | 5/2003 | Hoppe | G01J 3/04 356/445 |
| 7,245,370 B2* | 7/2007 | Bratkovski | G01N 21/658 356/301 |
| 7,749,765 B2 | 7/2010 | Demas et al. | |
| 8,183,049 B2 | 5/2012 | Kayano et al. | |
| 2006/0170918 A1* | 8/2006 | Nishiuma | G01N 21/553 356/318 |
| 2006/0209413 A1* | 9/2006 | Kim | B82Y 20/00 359/577 |
| 2014/0002111 A1* | 1/2014 | Potyrailo | H05K 1/16 324/655 |

FOREIGN PATENT DOCUMENTS

| | | |
|---|---|---|
| CN | 102519924 A | 6/2012 |
| CN | 103245652 A | 8/2013 |
| CN | 103305622 A | 9/2013 |
| CN | 103728264 A | 4/2014 |
| CN | 103940949 A | 7/2014 |
| CN | 104212804 A | 12/2014 |
| CN | 104267076 A | 1/2015 |
| CN | 104655578 A | 5/2015 |

OTHER PUBLICATIONS

Huang et al. Synthesis of semiconducting polymer microparticles as soild ionophore with abundant complexing sites for long-life Pb(II) sensors, ACS Applied Materials & Intrface, vol. 6, 2014, pp. 22096-22107.

Y. Xiao, et al., "Electrochemical detection of parts-per-billion lead via an electrode-bound DNAzyme assembly", Journal of the American Chemistry Society, vol. 129, 2007, pp. 262-263.

H. Z. He et al., "Label-free detection of sub-nanomolar lead(II) ions in aqueous solution using a metal-based luminescent switch-on probe", Biosensors and Bioelectronics, vol. 41, 2013, pp. 871-874.

Z. D. Wang et al., "Label-free colorimetric detection of lead ions with a nanomolar detection limit and tunable dynamic range by using gold nanoparticles and DNAzyme", Advanced Materials, vol. 20, 2008, pp. 3263-3267.

L. Jarup, "Hazards of heavy metal contamination", British Medical Bulletin, vol. 68, 2003, pp. 16-182.

L. Cui et al., "Electrochemical sensor for lead cation sensitized with a DNA functionalized prophyrinic metal-organic framework", Analytical Chemistry, vol. 87, 2015, pp. 10635-10641.

Y. Shi et al., "Ultrasensitive, specific, recyclable, and reproducible detection of lead ions in real systems through a polyadenine-assisted, surface-enhanced Raman scattering silicon chip", Analytical Chemistry, vol. 88, 2016, pp. 3723-3729.

Integrated DNA Technologies, Oligonucleotide Stability Study, 2014, http://www.idtdna.com/pages/docs/default-source/technical-reports/stability-guidance-external_final.pdf?sfvrsn=2.

J. Homola, "Surface Plasmon Resonance Sensors for Detection of Chemical and Biological Species", Chemical Reviews, vol. 108, 2008, pp. 462-493.

D.G. Myszka, Kinetic analysis of macromolecular interactions using surface plasmon resonance.

* cited by examiner

OPTOCHEMICAL DETECTOR AND A METHOD FOR FABRICATING AN OPTOCHEMICAL DETECTOR

TECHNICAL FIELD

This invention relates to an optochemical detector and a method for fabricating an optochemical detector, although not exclusively, to an optochemical detector for a detection of trace lead ion Pb(II) in water using label-free localized surface plasmon resonance (LSPR) and optical interferometry.

BACKGROUND

Pollution is one of the most serious public health problems in cities around the world. Various pollutants or containments in water may affect the health of the general public. Therefore, the quality of water must be regularly examined to ensure that some poisonous or hazardous pollutants do not exceed safety levels.

The concentration of these pollutants may be determined by using testing agents. The traditional chemical testing approaches are time consuming and may not respond promptly. Alternatively, material characterization techniques in laboratories may be used to analyze the concentration of a target substance and even the composition of a testing sample. Although the results may be very accurate and sensitive, these techniques used in laboratories may not be suitable for daily applications which require prompt and low-cost testing results.

SUMMARY OF THE INVENTION

In according with a first aspect of the present invention, there is provided an optochemical detector comprising: a light generation unit arranged to emit a light signal; a probe cell unit arranged to alter at least one physical characteristic of the light signal in response to an interaction with a target substance; and a light detection unit arranged to receive the light signal altered by the probe cell unit; wherein a detection of the target substance is characterized by a change in the at least one physical characteristic altered by the probe cell unit.

In an embodiment of the first aspect, wherein the at least one physical characteristic includes at least one of a phase and a resonance of the light signal.

In an embodiment of the first aspect, the probe cell unit comprises a localized surface plasmon resonance interferometer.

In an embodiment of the first aspect, the localized surface plasmon resonance interferometer includes a plurality of metal islands formed on a substrate.

In an embodiment of the first aspect, the plurality of metal islands comprises at least one material of gold, silver, copper and aluminum.

In an embodiment of the first aspect, each of the plurality metal islands includes a size of 100 nm to 150 nm.

In an embodiment of the first aspect, the localized surface plasmon resonance interferometer is arranged to introduce a change of the phase of the light signal.

In an embodiment of the first aspect, the probe cell unit comprises an ion-selective unit arranged to selectively interact with the target substance.

In an embodiment of the first aspect, the ion-selective unit is arranged to change a local refractive index of the probe cell unit.

In an embodiment of the first aspect, the resonance of the light signal is changed in response to the change in the local refractive index of the probe cell unit.

In an embodiment of the first aspect, the ion-selective unit includes an ionophore receptor arranged to selectively bind with the target substance.

In an embodiment of the first aspect, the ionophore receptor includes poly(m-phenylenediamine-co-Aniline-2-sulfonic acid).

In an embodiment of the first aspect, the probe cell unit further comprises a single channel or a multichannel microfluidic flow cell arranged to transfer the target substance to the ion-selective unit.

In an embodiment of the first aspect, the probe cell unit comprises a prism arranged to reflect the light signal.

In an embodiment of the first aspect, the light generation unit comprises a light source, an optical path correction unit and a light polarizer.

In an embodiment of the first aspect, the light source includes a polychromatic source; and wherein the light signal includes a continuous spectral energy distribution.

In an embodiment of the first aspect, the light source includes at least one of a quartz tungsten halogen lamp, a white-light emitting diode, a broadband superluminescent diode, a supercontinuum generated by propagation of ultrashort laser pulses in a microstructured optical fiber.

In an embodiment of the first aspect, the light polarizer includes a broadband linear polarizer.

In an embodiment of the first aspect, the optical path correction unit includes a broadband retardation crystal.

In an embodiment of the first aspect, the light detection unit comprises a linear array detector arranged to record an output result associated with a spectral interference fringe.

In an embodiment of the first aspect, the light detection unit further comprises a spectrometer arranged to resolve the spectral interference fringe.

In an embodiment of the first aspect, the light detection unit further comprises a monochromator arranged to resolve the spectral interference fringe.

In an embodiment of the first aspect, the light source includes a monochromatic source, wherein the light signal includes a narrow-band spectral energy distribution.

In an embodiment of the first aspect, the light source includes at least one of a single color laser, a tunable laser, single color light emitting diode in combination with a holographic single color filter, a single color superluminescent diode and a tunable single color superluminescent diode.

In an embodiment of the first aspect, the light polarizer includes a narrow-band linear polarizer.

In an embodiment of the first aspect, the optical path correction unit includes a quarter waveplate for an incident wavelength of the light signal.

In an embodiment of the first aspect, the light detection unit comprises a two dimensional imaging matrix detector arranged to record an output result associated with a spatial carrier fringe.

In an embodiment of the first aspect, the light detection unit further comprises a piezoelectric transducer arranged to alter an axial position of the light signal with respect to the light source, so as to introduce the spatial carrier fringe to the light signal.

In an embodiment of the first aspect, the target substance includes lead ion.

In according with a second aspect of the present invention, there is provided a method of fabricating an optochemical detector, comprising the steps of: providing a light generation unit arranged to emit a light signal and a light detection unit arranged to receive the light signal; disposing a probe cell along an optical path defined by the light generation unit and the light detection unit, such that the probe cell is operable to alter the light signal; and wherein a detection of the target substance is characterized by a change in the at least one physical characteristic altered by the probe cell unit.

In an embodiment of the second aspect, the at least one physical characteristic includes at least one of a phase and a resonance of the light signal.

In an embodiment of the second aspect, the probe cell unit comprises a localized surface plasmon resonance interferometer.

In an embodiment of the second aspect, the method further comprises the steps of fabricating the localized surface plasmon resonance interferometer by: depositing a layer of gold on a substrate; and annealing the substrate and the layer of gold to define a plurality of gold islands on the substrate.

In an embodiment of the second aspect, the substrate and the layer of gold is annealed at 550° C. for 3 hours.

In an embodiment of the second aspect, the probe cell unit comprises ion-selective unit.

In an embodiment of the second aspect, the method further comprises the steps of fabricating the ion-selective unit by: mixing a plurality of monomer of m-phenylenediamine with a plurality of monomer of aniline-2-sulfonic acid to form a co-monomer solution; preparing an oxidant solution by dissolving ammonium persulfate in hydrochloric acid; and mixing the oxidant solution with the co-monomer solution to form a co-polymer solution; wherein the co-polymer solution includes poly(m-phenylenediamine-co-Aniline-2-sulfonic acid).

In an embodiment of the second aspect, the method further comprises the steps of: functionalizing the localized surface plasmon resonance interferometer by submersing the localized surface plasmon resonance interferometer into the co-polymer solution; and combining the localized surface plasmon resonance interferometer with a prism arranged to reflect the light signal.

DETAILED DESCRIPTION OF THE INVENTION

Figure 1A:
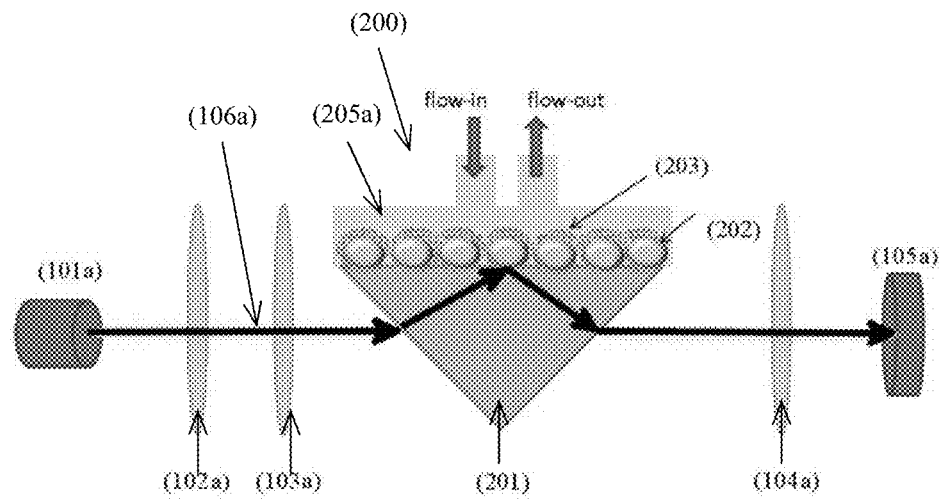
FIG. 1a is a block diagram of an optochemical detector according to a first embodiment of the present invention.

The inventors have, through their own research, trials and experiments, devised that detecting trace lead ion Pb(II) in water can be classified into three general categories, 1) electrochemistry, 2) luminescence and 3) colorimetry. Some of these involve additives to produce the transducer signal. For example, an iridium complex may be included for luminescence detection and DNAzyme may be included for colorimetric detection with gold nanoparticles.

However, it is preferable that "label-free" sensing of Pb(II) ions should not involve any additives to the sample under test and the concentration of Pb(II) ions in water should be quantitatively determined in its natural form. Besides, the overall test procedure should be rapid and involves as little sample preparation as possible. The test equipment should be compact and portable, so that on-site detection and quantification of Pb(II) in tap water can be performed immediately.

In addition, different Pb(II) sensing technique may be benchmarked in terms of 1) limit of detection (LOD), 2) linear range of response, and 3) specificity and 4) materials cost. The WHO guideline states that 10 ppb or 48 nM of Pb(II) in drinking water as the maximum threshold for daily consumption. On the other hand, the United States Environmental Protection Agency (U.S. EPA) demands less than 72 nM or 15 ppb of Pb(II) in portable water. Some example Pb(II) sensing performances are summarized in below table.

| Pb(II) detection | LOD | Linear range | Specificity | Material |
|---|---|---|---|---|
| Example 1 Electrochemistry | 0.034 nM | 0.05~200 nM | High | DNA + MOF |
| Example 2 Luminescence | 0.600 nM | 0.60~2.50 nM | High | DNA + Iridium |
| Example 3 Colorimetry | 3.000 nM | 1.00~100 nM | High | DNAzyme + nanogold |

The first row shows an LOD using a first example method of electrochemistry. In order to achieve such sensitivity, the sample solution was incubated with hairpin DNA ligand at elevated temperature of 37° C., then a catalytic metal-organic framework (MOF) as well as an oxidation agent were added to induce the measurable electrical signal of nanoampere. With these modifications, LOD of the electrochemical sensors was improved from nanomolar to semi-picomolar.

Another DNA specifically designed to capture Pb(II) ion was employed to produce the G-quadruplex conformation for enhancing the luminescence emission of an iridium probe. However, such performance of the luminescence sensor was only achieved at pH value of 8.2, which is not available as the pH value of tap water is about 7.

The colorimetric technique is a straightforward approach. The concentration of Pb(II) is directly proportional to the color change of the solution by the addition of a DNAzyme which modifies the inter-particle distance among gold nanoclusters. Thus, the optical extinction and color change can be measured and correlated with the Pb(II) concentration. However, LOD of the colorimetric detection is in the range of nanomolar, thus it is inferior to the two methods discussed previously.

In addition to these three general categories, surface enhanced Raman scattering (SERS) technique may be applied, which enables Pb(II) detection to about 0.009 nM (or 9 pM) and its linear range, i.e. the concentration range at which detection can be done, covers 10 pM to 1 uM, which spans over 6 orders of magnitude. A DNAzyme tagged with a Raman dye was required to capture Pb(II) and the DNAzyme was split to release the Raman dye so that SERS signal can be detected with the presence of Pb(II) ions.

According to the above table, DNA oligonucleotide plays the vital role in these example Pb(II) sensors. However, there may be certain general rules that govern the usage of DNA materials and some of these restrictions impede these techniques being employed for on-site operation.

Most DNA oligonucleotides are preferable to be kept at −20° C. for long term storage of up to 2 years. If the storage temperature is raised to 37° C., the storage duration is reduced dramatically to 6 weeks. Besides, a Tris-EDTA (TE) buffer at pH 8 is recommended to maintain the DNA stability. However, if water is used as buffer, DNA stability will be reduced.

In accordance with an embodiment of the present invention, inorganic materials may be employed to synthesize ionophore receptors for capturing Pb(II) ions in aqueous condition without involving DNA materials. By eliminating the oligonucleotide, the storage and operational conditions of the synthetic receptor are much less demanding and so the robustness and durability for on-site Pb(II) monitoring will be improved. Besides, TE buffer is not required for the synthetic receptor, so the materials cost can be further reduced.

Preferably, surface plasmon resonance (SPR) is a label-free sensing technique which may be applied to detection of biological and chemical species. However, in some particular conditions, SPR may not be suitable for label-free detection of Pb(II) due to a number of reasons, such as, 1) SPR device based on thin-film technology is limited to detection of specimen with molecular mass greater than 200 g/mol while that of Pb is about 207 g/mol, 2) SPR transducers based on angular and intensity interrogations are not sensitive enough to detect the localized refractive index change on adsorption of Pb(II) ions.

In accordance with the embodiments of the present invention, it is provided with an optochemical detector with subnanomolar (i.e. 0.15 ppb) detection limit to Pb(II) in a label-free manner. Such detection limit is two orders of magnitude better than the WHO guideline. Besides, no DNA oligonucleotide is involved so that the material and operational cost of the present invention is much reduced, for practical on-site Pb(II) detection and monitoring.

The present invention and various advantages thereof will be described with reference to exemplary embodiments in conjunction with the drawings.

Figure 1B:
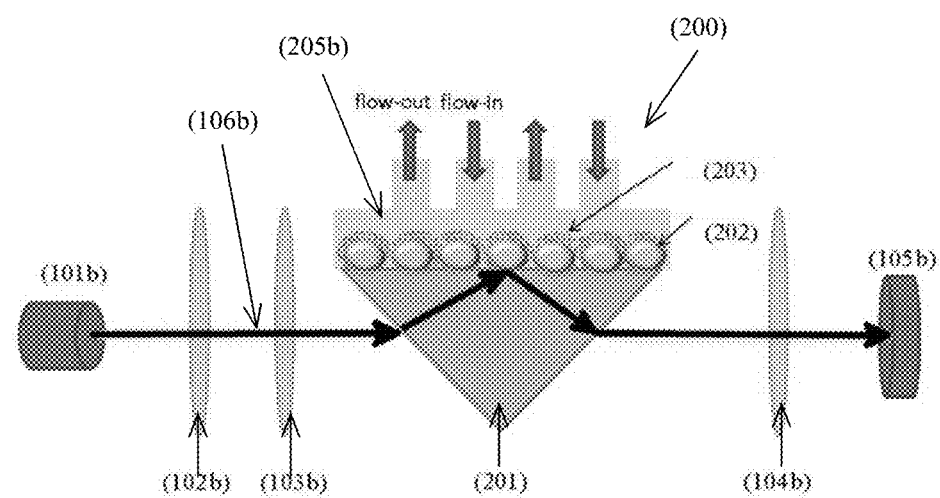
FIG. 1b is a block diagram of an optochemical detector according to a second embodiment of the present invention.

With reference to FIGS. 1a and 1b, there is provided an example embodiment of an optochemical detector 100 comprising: a light generation unit 101 arranged to emit a light signal 106; a probe cell unit 200 arranged to alter at least one physical characteristic of the light signal 106 in response to an interaction with a target substance; and a light detection unit 105 arranged to receive the light signal 106 altered by the probe cell unit 200; wherein a detection of the target substance is characterized by a change in the at least one physical characteristic altered by the probe cell unit 200.

In this embodiment, the optochemical detector 100 is operable to detect an existence and/or a concentration of a target substance such as a chemical containing chemical particles or ions, including but not limited to metal ions. In a specific application, the optochemical detector 100 may be used to detect or determine a concentration of Pb(II) ion in a sample solution. Preferably, the concentration of the target substance is represented by a detectable change in one or more physical characteristic (such as the phase and/or the resonance) in a light signal 106. The change may be introduced by different concentration, thus by comparing the altered light signal 106 with the original source signal, the concentration of the target substance may be determined.

Preferably, the probe cell unit 200 may comprise a plurality of optical structures arranged to alter the physical characteristics of the light signal 106 received, including a localized surface plasmon resonance interferometer (LSPR). The LSPR may include a plurality of metal islands 202 formed on a substrate, preferably a transparent glass substrate, which are operable to introduce a change of phase of the light signal 106 in the probe cell unit 200. In one example embodiment, the metal islands 202 may contain gold, silver, copper, aluminum, an alloy of these metals or any other suitable metal which may form island with sizes in nanometer (such as 100-150 nm) according to different designs and/or performance requirements.

In one example embodiment, the probe cell 200 comprises of the self-assembly gold nanoislands (AuNIs) 202 which are responsible for the localized surface plasmon resonance (LSPR) as shown in both FIGS. 1a and 1b.

Preferably, these AuNIs 202 may be fabricated by magnetron sputtering of an ultra-thin layer of gold onto the glass substrate. The nominal initial deposition thickness was 5 nm, which is substantially less than the general thickness requirement of 50 nm for SPR sensors. Therefore, the initial gold deposition did not produce much plasmonic absorption. The gold-on-glass substrate was then thermally annealed at 550° C., i.e. near the Tg temperature of glass, for 3 hours. The color changed from pale green to dark pink indicating the formation of nanosize gold particles which is responsible of the plasmonic absorption. Surface morphology scan with atomic force microscope reveals that AuNIs of about 40 nm in diameter were randomly formed on the glass surface. The combination of initial gold thickness, thermal annealing temperature and duration contributes to the morphology of AuNIs and the refractive index sensitivity.

In an experiment carried out by the inventor, it is found that with the initial thickness of the gold layer being too thin (i.e. less than 5 nm), the AuNIs population is scanty and reduces the overall sensitivity. Contrastly, with initial thickness being too thick (i.e. more than 5 nm), the AuNIs starts to aggregate and the plasmonic effect vanishes. On the other hand, with annealing temperature too low, the AuNIs fails to form; with annealing temperature too high, the AuNIs start to embed into the glass substrate and reduce sensitivity. It is also devised by the inventor that the annealing duration depends on the temperature, i.e. the higher the temperature, the shorter the anealing duration. In one example embodiment, the optimized fabrication condition of AuNIs 202 is determined as 5 nm of initial gold deposition and thermally annealed at 550° C. for 3 hours.

In addition, the probe cell unit 200 may comprise an ion-selective unit arranged to selectively interact with the target substance. For example, a (synthetic) ionophore receptor 203 may be included to selectively bind with the target substance (lead ion) such that a local refractive index of the probe cell unit 200 is changed according to the reaction between the ionophore receptors 203 and different amount/concentration of lead ions. By changing the local refractive index of the probe cell unit 200, the resonance of the light signal 106 may be changed accordingly in response to the change in the local refractive index. Preferably, the ionophore receptor 203 includes poly(m-phenylenediamine-co-Aniline-2-sulfonic acid) (mPD-co-ASA) to achieve a high sensitivity in a nanomolar range. Alternatively, material poly(m-phenylenediamine-co-2-hydroxy-5-sulfonic aniline) (mPD-co-HS) may be used for Pb(II) sensing in a micromolar range. Alternatively, other ionophore receptors or ion-selective unit may be included for detecting ions other than lead ions or for detecting other chemical substances.

Preferably, the ionophore receptors 203 or the mPD-co-ASA copolymer may comprise of the first monomer m-phenylenediamine and the second monomer aniline-2-sulfonic acid. In contrast, the copolymer of comprises the first monomer m-phenylenediamine and the second monomer 2-hydroxy-5-sulfonic aniline. Alternatively, it may comprise the first monomer 2-hydroxy-5-sulfonic aniline and the second monomer aniline. The molar ratio between the first and second monomer determines the ultimate Pb(II) sensing performance and it was found as 19:1 (mPD vs. ASA).

The mPD-co-ASA copolymer may be prepared by oxidative copolymerization of the first monomer mPD and the second monomer ASA. An example preparation procedure of the mPD-co-ASA copolymer is: 1) mPD (2.055 g, 19 mmol) and ASA (0.173 g, 1 mmol) were mixed in a glass flask which contained 75 mL of 1.0 M HCl. 2) Ammonium persulfate (4.564 g, 20 mmol) was dissolved separately in 25 mL of 1.0 M HCl to prepare an oxidant solution. 3) Both solutions of step 1 and 2 were placed in a water bath at 30° C. for 30 min. 4) The co-monomer solution of step 1 was then magnetically stirred at 500 rpm and the oxidant solution of step 2 were added drop wise into co-monomer solution of step 1 at a rate of 20 µL/s over a period of 30 min at 30° C. 5) The reaction mixture was continuously stirred in the 30° C. water bath for 24 hours, and then the resulting copolymer solution were centrifuged at 2000 rpm for 15 minutes. The supernate solution with short-chained copolymer mPD-co-ASA 203 are utilized to functionalized the AuNIs 202 as lead ions receptors.

Figure 2A:
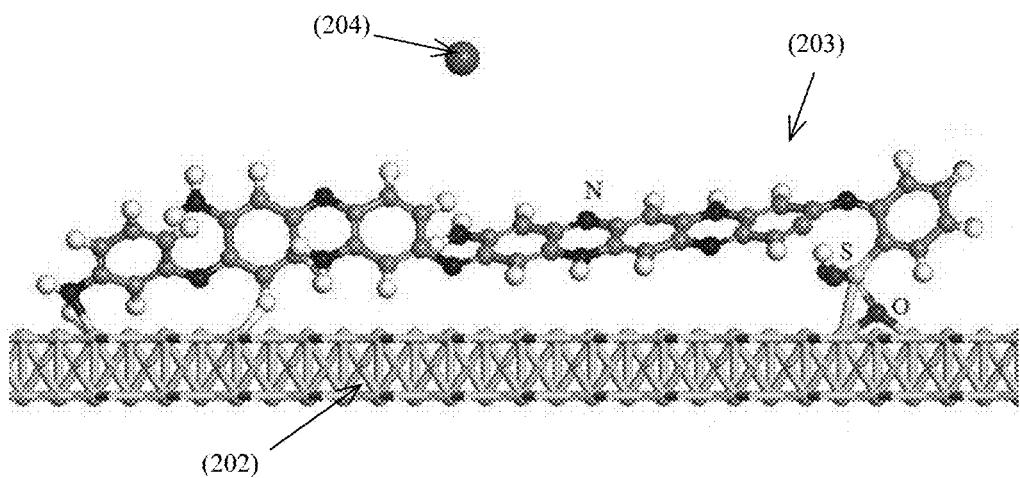
FIG. 2a is an illustration of a portion of the copolymer poly(m-phenylenediamine-co-Aniline-2-sulfonic acids) (mPD-co-ASA) functionalized on the surface of the gold nanoislands (AuNIs) before capture of the Pb(II) ion as shown in FIG. 1.
Figure 2B:
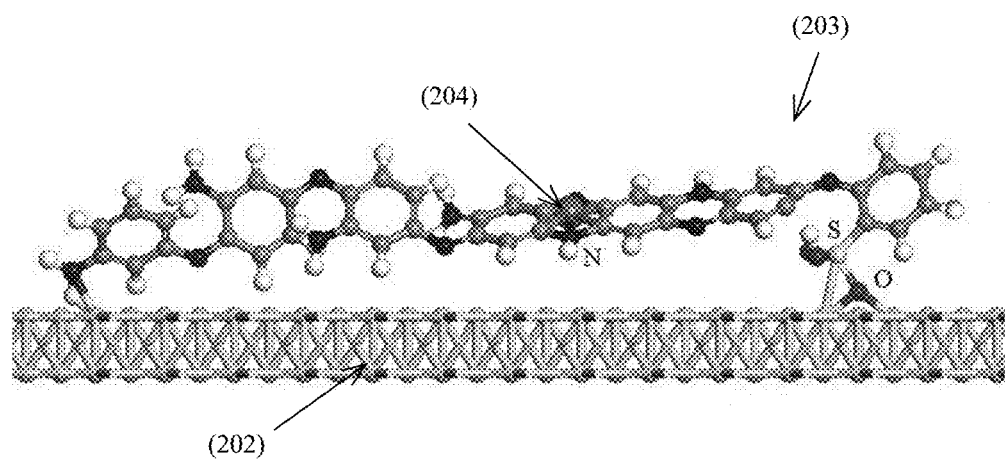
FIG. 2b is an illustration of a portion of the copolymer poly(m-phenylenediamine-co-Aniline-2-sulfonic acids) (mPD-co-ASA) functionalized on the surface of the gold nanoislands (AuNIs) after capture of the Pb(II) ion as shown in FIG. 1.

With reference to FIGS. 2A and 2B, there is shown an mPD-co-ASA functionalized gold surface (of a metal island 202) before capture of the Pb(II) ion and an mPD-co-ASA functionalized gold surface after capture of the Pb(II) ion respectively. In an interaction between the target substance 204 and the probe cell unit 200, the Pb(II) ion 204 binds to the NH₂ functional group of the short-chained copolymer and the SO₃H group attaches onto the gold surface 202 by the sulfur-gold bond. In a preferable embodiment, the short-chained mPD-co-ASA copolymer extracted from the supernatant solution was employed for Pb(II) ion sensing, which may be different from other examples that co-polymer microparticles may be precipitated after centrifugation was used. The oxidative co-polymerization of this embodiment is illustrated in the oxidative co-polymerization of mPD-co-ASA scheme illustrated below and the LSPR sensing chips 202 were fully submersed into the supernatant solution and incubated at 30° C. for 24 hours before installing onto the TIR prism 201.

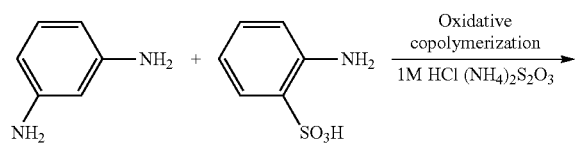

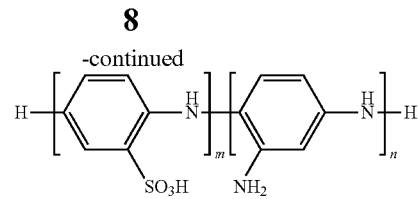

In this embodiment, the probe cell unit 200 further comprises a single channel 205a or a multichannel 205b microfluidic flow cell or channel arranged to transfer the target substance to the ion-selective unit. The micro-fluidic channel 205 is arranged to bring samples such as water samples into contact with the ionophore receptors 203 and facilitate the interaction between the target substance 204 and the probe cell unit 200.

Referring to FIG. 1A, the probe cell 200 further comprises of a single channel microfluidic channel 205a to bring Pb(II) ions in contact with the mPD-co-ASA receptors 203 on the AuNIs 202. Referring to FIG. 1B, the probe cell 200 further comprises of a multichannel microfluidic channel 205b to bring the Pb(II) into contact with the mPD-co-ASA receptors 203 on the AuNIS 202.

In addition, the probe cell unit 200 further comprises a prism 201 arranged to reflect the light signal 106. Preferably, the prism 201 does not introduce a change of phase and resonance of the light signal 106 passing through and being reflected, therefore the change introduced by the ion-selective structure 203 and the metal nanoislands 202 may be identified. Referring to FIGS. 1A and 1B, the probe cell 200 comprises of a total-internal-reflected prism (TIR prism) 201 which facilitates total internal reflection of the incident light. The TIR prism 201 should have high transmission in the visible spectrum. In one example embodiment, BK7 glass was employed for the TIR prism 201.

With reference to FIGS. 1A and 1B, the light generation unit 101 comprises a light source, and optical path correction unit and a light polarizer. Based on different designs and detection schemes, single channel or multichannel light signal 106 may be used for the detection of the target substance.

In a single channel operation example, the optical interference is generated in the spectral domain so a broadband light source with continuous spectral content is needed and a broadband retardation crystal is inserted to produce retardation (optical path difference) between the two orthogonal polarization components.

In this example, the light source 101a includes a polychromatic source; and wherein the light signal 106a includes a continuous spectral energy distribution. Examples of polychromatic source may include at least one of a quartz tungsten halogen lamp, a white-light emitting diode, a broadband superluminescent diode, a supercontinuum generated by propagation of ultrashort laser pulses in a microstructured optical fiber.

Besides, a broadband retardation crystal 103a is used as the optical correction unit. The retardation crystal 103a is arranged to bring sufficient and resolvable optical path difference between the orthogonal polarized TM and TE components in the altered light signal 106.

One or more polarizers 102, 104 may be included to process/filter the light signal 106. For example, a first polarizer 102 in the optical path before the probe cell unit 200 may be included to divide the incoming light into orthogonal polarized components, i.e. transverse magnetic (TM) and transverse electric (TE) components, and a second polarizer (an analyzer) 104 may be included to recombine the orthogonal polarized TM and TE components so the optical interference can be observed. Preferably, the light polarizers 102, 104 may be a pair of broadband linear polarizer for a single channel operation or a pair of narrow-band linear polarizer for a multichannel operation, and each pair of the polarizers should be of the same optical properties.

For detection of the altered light signal 106, in the single channel operation, the light detection unit 105 may comprise a linear array detector 105a arranged to record the output result associated with a spectral interference fringe. A spectrometer and/or a monochromator may also be included to resolve the spectral interference fringe in the altered light signal 106.

In the first example embodiment as illustrated in FIG. 1A, there is provided a Pb(II) sensor in accordance with the present invention of single channel detection. The optical interferometer 100a comprises: an white-light source unit 101a for providing a polychromatic beam of light with collimated output and a broadband linear polarizer 102a that convert randomly polarized light to linear polarization containing p- and s-polarized components; a broadband retardation crystal unit 103a to introduce optical path difference between the p- and s-polarized components; a broadband linear analyzer 104a recombines the p- and s-polarized components after traversing the total-internal-reflected (TIR) prism 201; a spectrometer 105a configured with sufficient resolution to resolve and record the spectral interference at the end of the optical path.

The polychromatic electromagnetic radiation source 101a may comprise a quartz tungsten halogen (QTH) lamp, a solid state white-light emitting diode (WLED), a broadband superluminescent diode (SLD), a supercontinuum generated by propagation of ultrashort laser pulses in a microstructured optical fiber or any other suitable polychromatic electromagnetic radiation source with a continuous broadband emission. Polychromatic sources with discrete broadband emission, i.e. high pressure Mercury lamp, are not suitable for this invention. The radiation source 101a is required to emit a beam of light containing random polarization components. In this embodiment, a WLED of 3 Watt is employed and its polarization is regarded as random.

The broadband polarizer 102a is designed for the visible range from 400 to 700 nm with extinction ratio at least 10,000:1. It may comprise a birefringent crystal, a dichroic plate, or a Brewster window. In this embodiment, a dichroic plate on glass substrate designed for 400 to 700 nm with extinction ratio of 10,000 to 1 was used. In this embodiment, the broadband analyzer 104a is built to the same specification as the broadband polarizer 102a; the analyzer comprises a birefringent crystal, a dichroic plate, or a Brewster window. In this embodiment, a dichroic plate on glass substrate designed for 400 to 700 nm with extinction ratio of 10,000:1 was used as the analyzer.

The retardation crystal 103a is designed to introduce sufficient and resolvable retardation between the ordinary ray and extra-ordinary ray traversing the crystal, and the ordinary ray and extra-ordinary ray were aligned with the p- and s-polarized components from the polarizer 102a respectively. Thus, the retardation was applied to the polarized components. In this embodiment, an undoped yttrium vanadate ($YVO_4$) crystal of customized thickness was employed. It is found that the thickness of the crystal plays a critical role in the sensitivity of the sensor. With increasing thickness of the crystal, the retardation length increases. Thus, the spectral interference density increases, leading to higher phase resolution and better sensitivity. However, this is achieved only if the spectrometer 105a fully resolves the spectral interference. Therefore, the crystal thickness has to be optimized with the spectrometer resolution. In this embodiment, the spectrometer resolution is about 0.1 nm and the $YVO_4$ thickness is determined to be 630 micrometer.

Alternatively, in a multichannel operation, the optical interference is generated in the spacial domain so a monochromatic light source 101b with narrow-band spectral content is needed and a quarter wave-plate 103b is needed to produce retardation (optical path difference) between the two orthogonal polarization components.

In this example, the light source 101b may include a monochromatic source, wherein the light signal 106b may include a narrow-band spectral energy distribution. Examples of monochromatic source 101b may include at least one of a single color laser, a tunable laser, single color light emitting diode in combination with a holographic single color filter, a single color superluminescent diode and a tunable single color superluminescent diode.

Besides, a quarter waveplate 103b is used as the optical correction unit. The quarter waveplate 103b is arranged to bring ¼ optical path difference between the orthogonal polarized TM and TE components of the incoming light wave.

Similar to the single channel operation, one or more polarizers 102b, 104b may be included to process/filter the light signal 106b, i.e. a pair of narrow-band linear polarizer for a multichannel operation may be included in the optical path before and after the probe cell unit 200.

For detection of the altered light signal 106, in the multichannel operation, the light detection unit 105b may comprise a two dimensional imaging matrix detector arranged to record an output result associated with a spatial carrier fringe. The light detection unit 105b may further comprise a piezoelectric transducer arranged to alter an axial position of the light signal 106b with respect to the light source, so as to introduce the spatial carrier fringe to the light signal 106b.

In the second example embodiment as illustrated in FIG. 1B, there is provided Pb(II) sensor in accordance with the present invention of multichannel detection. The optical interferometer 100b comprises: a monochromatic source unit 101b for providing a beam of single color light with collimated output and a narrow-band linear polarizer 102b that converts randomly polarized light to linear polarization containing p- and s-polarized components; a narrow-band retardation crystal unit 103b to introduce optical path difference between the p- and s-polarized components; a narrow-band linear analyzer 104b recombines the p- and s-polarized components after traversing the total-internal-reflected (TIR) prism 201; an imaging matrix detector 105b configured with sufficient resolution to resolve and record the spatial interference at the end of the optical path.

The monochromatic electromagnetic radiation source 101b may comprise a single color laser, a tunable laser, solid state single color light emitting diode (LED) in combination with a holographic single color filter, a single color superluminescent diode (SLD), a tunable single color SLD, or any other suitable monochromatic electromagnetic radiation source with a narrow-band emission. The radiation source 101b is a beam of light containing either random or linear polarization components. In this embodiment, a 7 Watt red LED emitting at 623 nm with a holographic filter of 1 nm full-width-half-maximum (FWHM) bandwidth at 623 nm is employed and its polarization is regarded as random.

The narrow-band polarizer 102b is designed for the visible range from 400 to 700 nm with extinction ratio of at least 10,000:1. It may comprise a birefringent crystal, a dichroic plate, or a Brewster window. In this embodiment, a dichroic plate on glass substrate designed for 400 to 700 nm with extinction ratio of 10,000 to 1 was used. In this embodiment, the narrow-band analyzer 104b is built to the same specification as the narrow-band polarizer 102b, the analyzer comprises a birefringent crystal, a dichroic plate, or a Brewster window. In this embodiment, a dichroic plate on glass substrate designed for 400 to 700 nm with extinction ratio of 10,000:1 was used as the analyzer.

The retardation crystal 103b is designed to introduce a quarter of pi ($\lambda/4$) retardation between the ordinary ray and extra-ordinary ray traversing the crystal, and the ordinary ray and extra-ordinary ray were aligned with the p- and s-polarized components from the polarizer 102b respectively. Thus, a quarter of pi retardation was applied to the polarized components. In this embodiment, a $\lambda/4$ achromatic wave-plate designed for 610 to 850 nm was employed to accommodate the LED wavelength of 623 nm. An imaging matrix sensor, e.g. CCD or 2D photodiode array can be employed to record the spatial interference signal. In this embodiment, a monochromatic CCD camera with 16 bit gray level resolution was employed. For improved phase detection, the multichannel configuration further comprises a piezoelectric (PZT) transducer to alter the axial position of the LED source. In this embodiment, the PZT is shown in FIG. 1b to include spatial carrier fringes for improved interferometric phase processing.

In an example operation of the optochemical detector 100, to detect Pb(II) ions in a specimen, the SAM-AuNIs LSPR chip may be first functionalized by submersion into the mPD-co-ASA solution in a water bath at 30° C. for 24 hours, the prepared chip is then installed on the TIR prism so that the functionalized SAM-AuNIs interact with the evanescent field of the TIR light. The installed chip is coupled with the microfluidic inlets and outlet to complete the probe cell. Deionized water buffer is injected at flow rate of 0.5 milliliter per minute to establish a steady baseline for 100 seconds. After that, aqueous Pb(II) specimen may be injected into the probe cell at the same flow rate of 0.5 milliliter per minute for 500 seconds. Finally, deionized water buffer is injected at the same flow rate of 0.5 milliliter per minute for 100 seconds to rinse non-specifically bound ions to the mPD-co-ASA receptors.

In another example operation of the optochemical detector 100, to rapidly detect concentration of Pb(II) ions, a buffer of 0.8 milliliter deionized water may be added to establish the Pb(II) ion free baseline, a raw specimen solution of 4 milliliter may be used to determine the Pb(II) ion concentration. Finally, a buffer of 0.8 milliliter deionized water may be used to confirm the concentration of Pb(II) ion. In this operation, the total test time is 12 minutes with flow rate of 0.5 milliliter per minute, or the total test time is 6 minutes with flow rate of 1 milliliter per minute.

The flow rates of the above examples are different. With slow flow rate at 10 to 50 uL/min which is the typical flow rate of standard surface plasmon resonance experiment, the mPD-co-ASA ionophore receptors show relatively high affinity to other ions, i.e. mercury Hg(II). So its selectivity to Pb(II) was diminished. However, with flow rate increased to 200 uL/min, the affinity to Hg(II) decreased with LSPR phase recovered to its initial value, whereas the LSPR phase increment due to Pb(II) was unaltered at the same flow rate.

These embodiments may be advantageous in that the optochemical detector may provide up to ppb-level sensitivity of target substance, which may be useful in applications such as detecting trace lead ion Pb(II) in water, in particular Pb(II) ions concentration of about 10 part-per-billion (ppb) which is the safety threshold of drinking water specified by the World Health Organization (WHO) using label-free localized surface plasmon resonance (LSPR) and optical interferometry.

Advantageously, the optochemical detector is based on a label-free detection with the ion-selection structure realized by the synthetic ionophore receptors in the probe cell unit, therefore, no DNA materials are needed. In addition, the probe cell unit is highly-selective to the target substance only, and does not require any amplification additives. The detector structure is also simple, which allow these optochemical detectors to be produced as compact devices with excellent robustness and portability.

Figure 3:
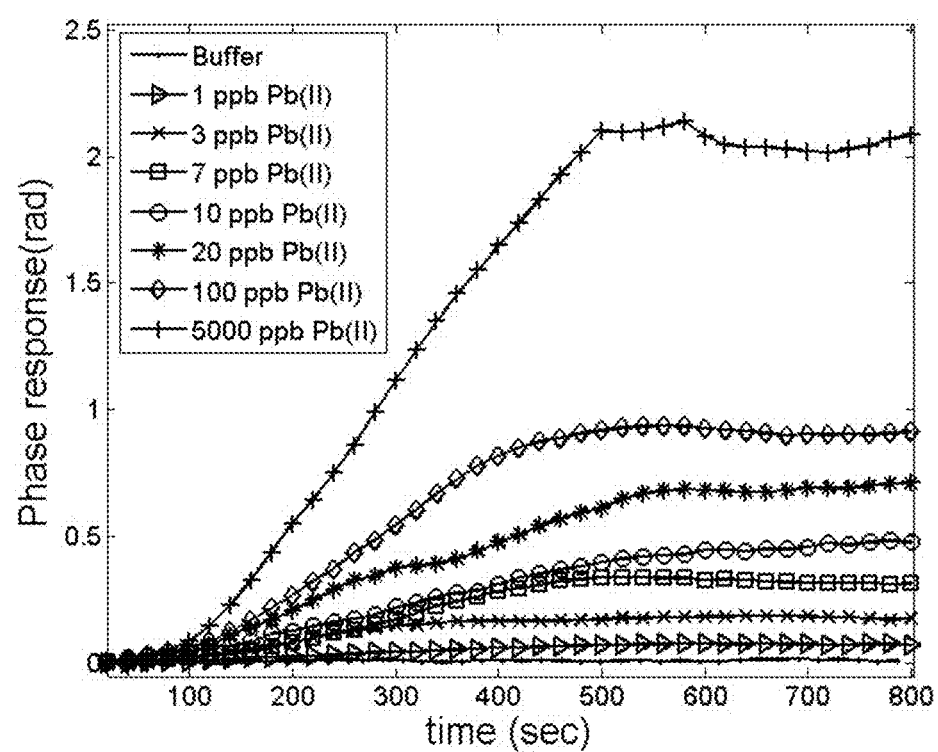
FIG. 3 is the phase responses of the LSPR interferometric sensor to Pb(II) ions of various concentration from 1 ppb to 5 ppm and the response to buffer control is also included.

The phase datagram of the present invention as detection of Pb(II) of various concentration is shown in FIG. 3. The Pb(II) solutions were obtained by dissolving $Pb(NO_3)_2$ of 10 milligrams weighted mass into 1 liter of 18.2 megohm deionized water. The seed solution of 10 ppm (10,000 ppb) Pb(II) was repeatedly diluted with deionized water to obtain Pb(II) concentration of 1, 3, 7, 10, 20, 100 and 5,000 ppb. The sensing procedure was performed with the deionized water as buffer for the first 100 seconds at the flow rate of 0.5 milliliter per minute. Then, the Pb(II) solution was injected at the same flow rate from the 101 second to the 500 second. The deionized water was injected again at the same flow rate from the 501 second to the 800 second. By observation of FIG. 3, it is obvious that the phase response of the LSPR interferometer increases in accordance to the Pb(II) ion concentration. The phase datagram maintains its final value even with flushing by the buffer. This is an indication that Pb(II) was firmly adsorbed by the mPD-co-ASA copolymer so that the phase datagram remains unchanged. The entire sensing procedure is completed in about 10 minutes.

Figure 4:
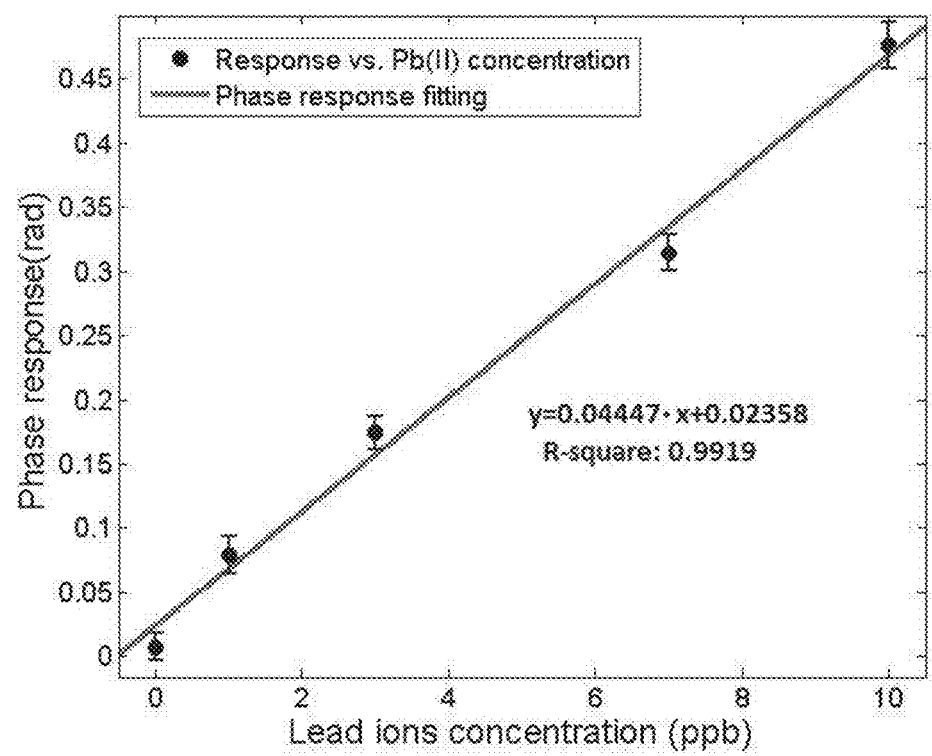
FIG. 4 is the linear regression fitting to the phase data of relatively low Pb(II) concentration and the fitted linear equation was used to estimated LOD of the present invention.

To determine the limit of detection (LOD) of the optochemical detector in accordance to the embodiment of the present invention, the phase measurement was repeated at least 3 times for the buffer, 1, 3, 7, and 10 ppb of Pb(II) and the phase response was plotted against the Pb(II) ion concentrations as shown in FIG. 4. The linear regression fitted equation was found as $y=0.04447*x+0.02358$ (R-square=0.9919). This is used to calculate the LOD according to the definition by the International Union of Pure and Applied Chemistry. This gives the LOD of 0.15 ppb, which is two orders of magnitude better than the WHO allowable threshold.

Figure 5:
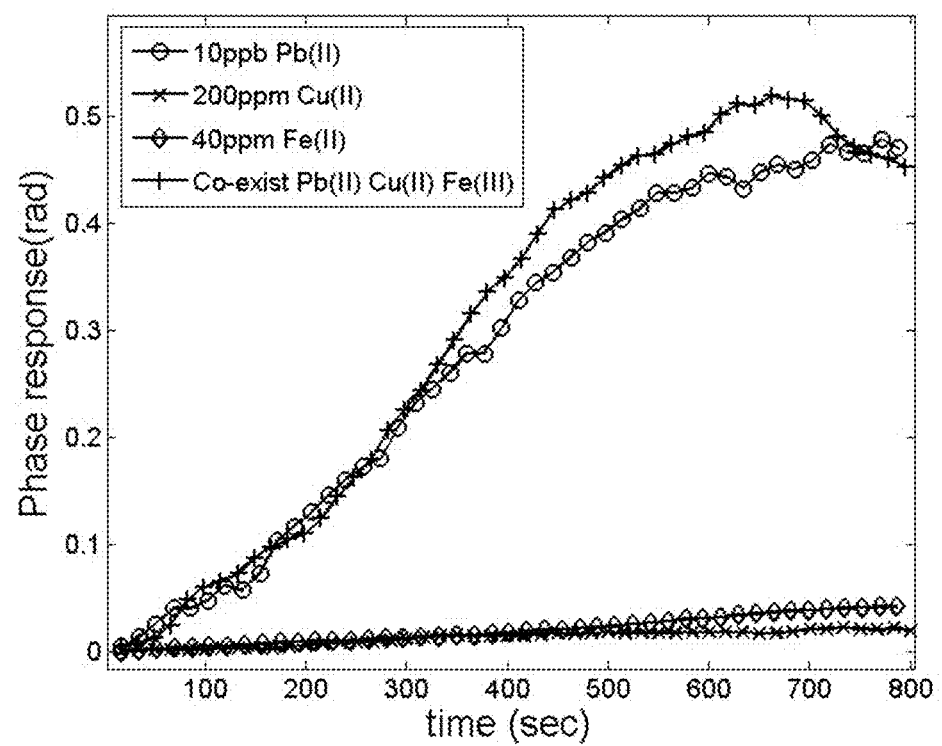
FIG. 5 is the phase responses of the LSPR interferometric sensor to 200 ppm Cu(II), 40 ppm Fe(III), ppb Pb(II) and the combination of the three ion concentrations.
Figure 6:
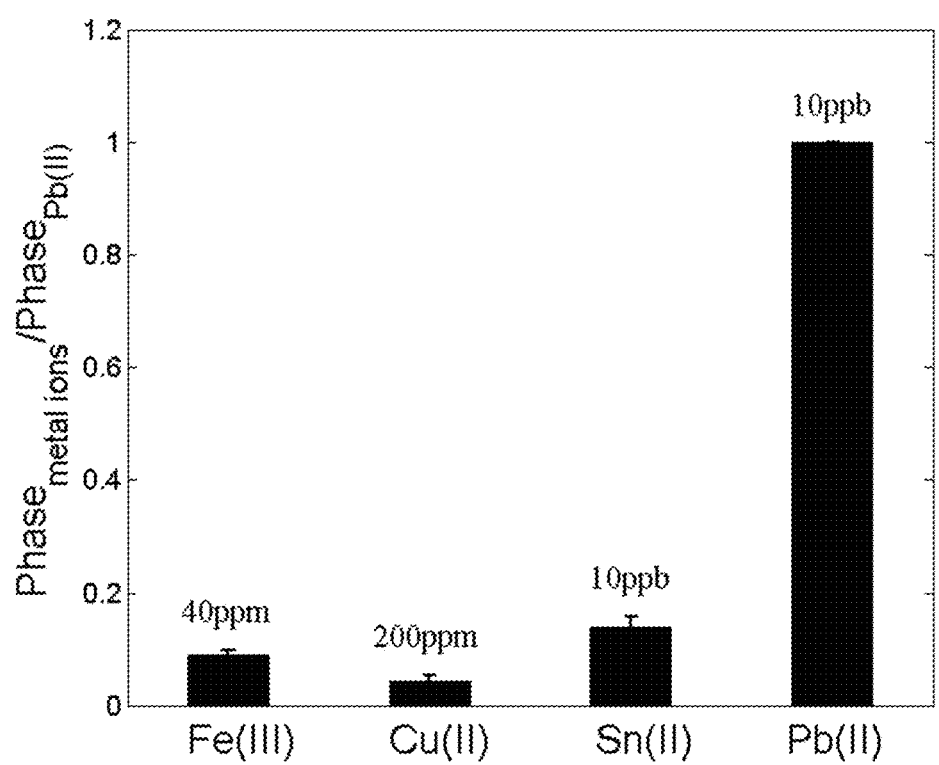
FIG. 6 is the selectivity of the poly(m-phenylenediamine-co-Aniline-2-sulfonic acids) (mPD-co-ASA) receptor to 10 ppb Pb(II) in comparison to other metallic ions of various concentrations for the present invention.

To examine the selectivity for specific detection of Pb(II) ions, experiments with 200 ppm Cu(II) and 40 ppm Fe(II) were carried out by the inventors to simulate situations of copper and iron pipes are usually employed for transportation of drinking water. To accommodate the worse scenario, these ions, i.e. Pb(II), Cu(II) and Fe(II) of 10 ppb, 200 ppm and 40 ppm respectively, are introduced and are tested with the optochemical detector in accordance to the embodiment of the present invention. The resulting phase datagram is shown in FIG. 5. It can be seen that the system shows only marginal response to high concentrations of Cu(II) and Fe(II) since the mPD-co-ASA receptor is highly specific to Pb(II). The system maintains excellent selectivity to Pb(II) even in combination of high concentrations of Cu(II) and Fe(II) ions. With flushing of buffer starting at the 601 second in FIG. 5, the phase response of the combined solution drops back to the same level as 10 ppb Pb(II); this is due to the recovery of local refractive index surrounding the receptor by deionized water. The selectivity of the present invention was further benchmarked by comparison of the phase response of other ions of different concentrations, i.e. 40 ppm Fe(II), 200 ppm Cu(II) and 10 ppb Sn(II) against that of 10 ppb Pb(II) as shown in FIG. 6. The most important discovery shown in FIG. 6 is that the present invention shows remarkable immunity to Sn(II) ion which may impede the accuracy of colorimetric Pb(II) detection method.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. An optochemical detector comprising:
a light generation unit arranged to emit a light signal, wherein the light generation unit includes a monochromatic light source or a polychromatic light source;
a probe cell unit arranged to alter at least one physical characteristic of the light signal in response to an interaction with a target substance including lead ions; and
a light detection unit arranged to receive the light signal altered by the probe cell unit, wherein the light detection unit includes a two dimensional imaging matrix detector or a linear array detector;
wherein a detection of the target substance is characterized by a change in the at least one physical characteristic altered by the probe cell unit;
wherein the probe cell unit includes a layer of metal with a plurality of metal islands formed on a substrate and a plurality of ionophore receptors disposed on the plurality of metal islands, and a microfluidic flow cell arranged to transfer the target substance to the ionophore receptors, the plurality of ionophore receptors are arranged to selectively bind with the target substance so as to change a local refractive index of the probe cell unit at a region surrounding the ionophore receptors that bind with the target substance.

2. An optochemical detector in accordance with claim 1, wherein the at least one physical characteristic includes a phase of the light signal.

3. An optochemical detector in accordance with claim 2, wherein the probe cell unit comprises a prism arranged to reflect the light signal.

4. An optochemical detector in accordance with claim 1, wherein the at least one physical characteristic includes a resonance of the light signal.

5. An optochemical detector in accordance with claim 1, wherein the plurality of metal islands comprises at least one material of gold, silver, copper and aluminum.

6. An optochemical detector in accordance with claim 1, wherein each of the plurality metal islands includes a size of 100 nm to 150 nm.

7. An optochemical detector in accordance with claim 1, wherein the ionophore receptors that bind with the target substance on the plurality of metal islands in the probe cell unit are arranged to introduce a change of the phase of the light signal.

8. An optochemical detector in accordance with claim 1, wherein the ionophore receptor includes poly(m-phenylene-diamine-co-Aniline-2-sulfonic acid).

9. An optochemical detector in accordance with claim 1, wherein the microfluidic flow cell includes a single channel with a single inlet and a single outlet or includes a multi-channel with multiple inlets and multiple outlets.

10. An optochemical detector in accordance with claim 1, wherein the light generation unit further comprises an optical path correction unit and a light polarizer.

11. An optochemical detector in accordance with claim 10, wherein the light source includes a monochromatic source, wherein the light signal includes a narrow-band spectral energy distribution generated by the monochromatic light source.

12. An optochemical detector in accordance with claim 11, wherein the monochromatic light source includes at least one of a single color laser, a tunable laser, a single color superluminescent diode and a tunable single color superluminescent diode, or a single color light emitting diode and a holographic single color filter which combine to form the monochromatic source.

13. An optochemical detector in accordance with claim 11, wherein the light polarizer includes a narrow-band linear polarizer.

14. An optochemical detector in accordance with claim 11, wherein the optical path correction unit includes a quarter waveplate for an incident wavelength of the light signal.

15. An optochemical detector in accordance with claim 11, wherein the two dimensional imaging matrix detector is arranged to record an output result associated with a spatial carrier fringe.

16. An optochemical detector in accordance with claim 15, wherein the light detection unit further comprises a piezoelectric transducer arranged to alter an axial position of the light signal with respect to the light source, so as to introduce the spatial carrier fringe to the light signal.

17. An optochemical detector in accordance with claim 10, wherein the light signal includes a continuous spectral energy distribution generated by the polychromatic light source.

18. An optochemical detector in accordance with claim 17, wherein the polychromatic light source includes at least one of a quartz tungsten halogen lamp, a white-light emitting diode and a broadband superluminescent diode, or a ultra-short laser source and a microstructured optical fiber which combine to form the polychromatic source and arranged to generate a supercontinuum by propagating ultrashort laser pulses in the microstructured optical fiber.

19. An optochemical detector in accordance with claim 17, wherein the light polarizer includes a broadband linear polarizer.

20. An optochemical detector in accordance with claim 17, wherein the optical path correction unit includes a broadband retardation crystal.

21. An optochemical detector in accordance with claim 17, wherein the linear array detector is arranged to record an output result associated with a spectral interference fringe.

22. An optochemical detector in accordance with claim 21, wherein the light detection unit further comprises a spectrometer arranged to resolve the spectral interference fringe.

23. An optochemical detector in accordance with claim 22, wherein the light detection unit further comprises a monochromator arranged to resolve the spectral interference fringe.

24. A method of fabricating an optochemical detector, comprising the steps of:
providing a light generation unit arranged to emit a light signal and a light detection unit arranged to receive the light signal; and disposing a probe cell along an optical path defined by the light generation unit and the light detection unit, such that the probe cell is operable to alter the light signal, wherein the probe cell includes a plurality of ionophore receptors arranged to selectively bind with a target substance including lead ions;

wherein the light generation unit includes a monochromatic light source or a polychromatic light source;

wherein the light detection unit includes a two dimensional imaging matrix detector or a linear array detector;

wherein the probe cell unit includes a layer of metal defining with a plurality of metal islands formed on a substrate, a plurality of ionophore receptors disposed on the plurality of metal islands, and a microfluidic flow cell arranged to transfer the target substance to the ionophore receptors; and wherein a detection of the target substance is characterized by, upon applying the target substance to the ionophore receptors on the probe cell unit, observing a change in the at least one physical characteristic altered by the probe cell unit based on a change in a local refractive index of the probe cell unit at a region surrounding the ionophore receptors that bind with the target substance.

25. A method of fabricating an optochemical detector in accordance with claim 24, wherein the at least one physical characteristic includes a phase of the light signal.

26. A method of fabricating an optochemical detector in accordance with claim 25, wherein the at least one physical characteristic includes a resonance of the light signal.

27. A method of fabricating an optochemical detector in accordance with claim 24, further comprising the steps of fabricating the probe cell unit by:
    depositing a layer of gold on the substrate; and
    annealing the substrate and the layer of gold to define a plurality of gold islands on the substrate.

28. A method of fabricating an optochemical detector in accordance with claim 27, wherein the substrate and the layer of gold is annealed at 550° C. for 3 hours.

29. A method of fabricating an optochemical detector in accordance with claim 28, further comprising the steps of fabricating the plurality of ionophore receptors by:
    mixing a plurality of monomer of m-phenylenediamine with a plurality of monomer of aniline-2-sulfonic acid to form a co-monomer solution;
    preparing an oxidant solution by dissolving ammonium persulfate in hydrochloric acid; and
    mixing the oxidant solution with the co-monomer solution to form a co-polymer solution;
wherein the co-polymer solution includes poly(m-phenylenediamine-co-Aniline-2-sulfonic acid).

30. A method of fabricating an optochemical detector in accordance with claim 29, further comprising the steps of:
    functionalizing the probe cell by submersing the substrate with the layer of gold into the co-polymer solution; and
    combining the substrate with a prism arranged to reflect the light signal.

\* \* \* \* \*